US006835686B2

(12) United States Patent
Kolomeyer et al.

(10) Patent No.: US 6,835,686 B2
(45) Date of Patent: Dec. 28, 2004

(54) CATALYST SYSTEM AND PROCESS FOR REARRANGEMENT OF EPOXIDES TO ALLYLIC ALCOHOLS

(75) Inventors: Gennadiy G. Kolomeyer, Jacksonville, FL (US); Jacob S. Oyloe, Jacksonville, FL (US)

(73) Assignee: Millennium Specialty Chemicals, Jacksonville, FL (US)

( * ) Notice: Subject to any disclaimer, the term of this patent is extended or adjusted under 35 U.S.C. 154(b) by 192 days.

(21) Appl. No.: 09/899,518

(22) Filed: Jul. 5, 2001

(65) Prior Publication Data

US 2003/0065230 A1 Apr. 3, 2003

(51) Int. Cl.[7] .......................... C07C 29/56; C07C 35/06
(52) U.S. Cl. ........................ 502/102; 502/254; 536/4; 568/621; 568/300
(58) Field of Search ............................... 502/102, 254; 536/4; 568/300, 621

(56) References Cited

U.S. PATENT DOCUMENTS

| | | | |
|---|---|---|---|
| 2,426,264 A | | 8/1947 | Fowler et al. |
| 2,986,585 A | | 5/1961 | Denton |
| 4,496,776 A | | 1/1985 | Edwards et al. |
| 5,262,371 A | * | 11/1993 | Faraj ........................... 502/78 |
| 5,292,974 A | * | 3/1994 | Faraj ........................... 568/908 |
| 5,455,215 A | | 10/1995 | Faraj |
| 6,093,793 A | * | 7/2000 | Hofmann et al. ........... 528/411 |
| 6,180,726 B1 | * | 1/2001 | Eklund et al. .............. 525/408 |
| 6,335,304 B1 | * | 1/2002 | He et al. .................... 502/162 |
| 6,492,565 B2 | * | 12/2002 | Denninger et al. ......... 568/618 |
| 6,518,441 B2 | * | 2/2003 | Grosch et al. .............. 549/531 |
| 6,743,748 B2 | * | 6/2004 | Mizuno et al. ............. 502/254 |

FOREIGN PATENT DOCUMENTS

| | | | | |
|---|---|---|---|---|
| GB | WO 95/25079 A1 | * | 9/1995 | ........... C07C/29/56 |
| JP | 50/58031 | | 5/1975 | |
| JP | 11/49709 | | 2/1999 | |

OTHER PUBLICATIONS

Patent Abstracts of Japan, vol. 014, No. 211 (C0715), (May 2, 1990)–&–JP 02 047244 A (Furikawa Alum Co Ltd), (Feb. 16, 1990) abstract.
Michael B. Smith: "Organic Synthesis" 1994, McGraw–Hill XP002217490 p. 243–p. 245.
Hisashi Yamamoto: "A General Method for the Synthesis of 1,3–Dienes. Simple Syntheses of beta– and trans–alpha–Farnesene from Farnesol" Journal of the American Chemical Society, vol. 97, No. 11, (May 28, 1975), pp. 3252–3254, XP002217488, p. 3252, column 2——p. 3253; table I.

Kozo Tanabe et al: "Isomerization of d–Limonene Oxide over Aluminas" Chemistry Letters, 1976, pp. 321–322, XP001107272 *the whole document*.
John C. Leffingwell et al: "Reactions of Limonene 1,2–Oxides. I. The Stereospecific Reactions of the (+)–cis– and (+)–trans–Limonene 1,2 Oxides" Journal of Organic Chemistry, vol. 31, 1966, pp. 1937–1944, XP002217489 *the whole document*.
Arata, K. et al. Isomerization of d–Limonene Oxide Over Aluminas. *Chem. Letters* 321–322 (1976).
Bessiere, Y. et al. Isomerizatin of Limonene Epoxides, Allylic Rearrangement of p–Mentha–1(7),8–dien–2–ols: Preparation of Perilla Alcohol. *J. Chem. Res.* (S) 12:304–305 (1977).
Crandall, J.K. et al. Base–promoted Isomerizations of Epoxides. *Organic Reactions* 29:345–443 (1983).
de Graauw, C.F. et al. Meerwein–Ponndorf–Verley Reductions and Oppenauer Oxidations: An Integrated Approach. *Synthesis* 10:1007–1017 (1994).
Djerasse, C. The Oppenauer Oxidation. *Organic–Reactions* VI(5)207–272 (1951).
Eschinasi, E.H. The Aluminum Alkoxide Rearrangement of Epoxides, Part I: The Synthesis of Allylic Alcohols and Glycols Monoethers. *Isr. J. Chem.* 6:713–721 (1968).
Jayasree, J. Catalytic transformation of (–)–limonene oxide over binary oxide catalysts of alumina rare earths. *Ind. J. Chem.* 36A(9):765–768 (1997).
Pybus et al. The Chemistry of Fragrances, *The Royal Society of Chemistry* 4:68–69 (1999).
Smith. Synthetically Useful Reactions of Epoxides, *Synthesis* 8:629–656 (1984).
Tanabe, K. et al. Rearrangements of Epoxides Over Solid Acid and Base Catalysts, *Terpene Chemistry* 2.5:67–95 (1982).
Traynor, S.G. et al. Stereospecific rearrangements of monoterpene epoxides. *Proceedings of the VIII International Congress of Essential Oils* 591–594 (1980).

* cited by examiner

Primary Examiner—Mark L. Bell
Assistant Examiner—Jennine M Brown
(74) Attorney, Agent, or Firm—Needle & Rosenberg, P.C.

(57) ABSTRACT

A catalyst system comprising a primary catalyst chosen from one or more homogeneous or heterogeneous, inorganic, organic or complex metal-containing compound; and one or more phenolic activator/modifier(s). The catalyst system can be used for the preparation of allylic alcohols by rearrangement of corresponding epoxides, the subsequent Oppenauer type oxidation of allylic alcohols to alpha, beta-unsaturated carbonyl compounds, and/or the preparation of alpha, beta-unsaturated carbonyl compounds by rearrangement of epoxides to corresponding allylic alcohols followed by the subsequent Oppenauer type oxidation of allylic alcohols in a one pot process.

20 Claims, No Drawings

CATALYST SYSTEM AND PROCESS FOR REARRANGEMENT OF EPOXIDES TO ALLYLIC ALCOHOLS

FIELD OF THE INVENTION

The invention relates to the field of organic synthesis. Particularly, the invention relates to the rearrangement of epoxides as well as the preparation of allylic alcohols and alpha,beta-unsaturated carbonyl compounds, which find a wide spectrum of application in many areas of synthetic and industrial organic chemistry.

BACKGROUND OF THE INVENTION

Allylic alcohols are widely used in the chemical industry, for example, as flavor and fragrance ingredients. Moreover they can serve as intermediates, e.g., in the manufacture of alpha, beta-unsaturated carbonyl compounds by Oppenauer oxidation.

In general, the rearrangement of epoxides to allylic alcohols and further oxidation of obtained alcohols can be expressed as follows:

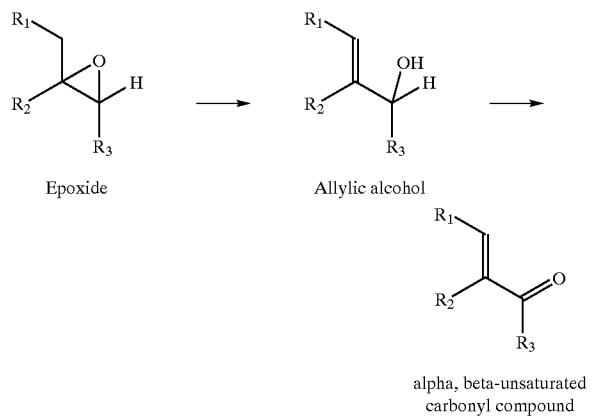

where $R_1$–$R_3$ represent hydrogen atom, alkyl, aryl, aralkyl groups, or together form a cycloalkyl group.

Traditional methods used for the rearrangement of epoxides to allylic alcohols include:

A. Stoichiometric Opening of the Epoxide Ring with Strong Bases:

See J. K. Crandall and M. Apparu, "Base-promoted Isomerizations of Epoxides" in: Organic reactions, John Wiley & Sons, Inc., New York, Chichester, Brisbane, Toronto, Singapore, 1983, Vol. 29, pp. 345–443 which is incorporated by reference in its entirety.

This method suffers from a number of disadvantages. For example, the use of at least stoichiometric amount or, in most reactions, a large excess of the expensive reagent (lithium amide, lithium diisopropylamide, butyl lithium, aluminum amides, potassium butoxide, etc.) is a major disadvantage of this method. In addition, when the epoxide ring opening may proceed in different directions, this method lacks the selectivity and flexibility to lead the process towards formation of a specific product.

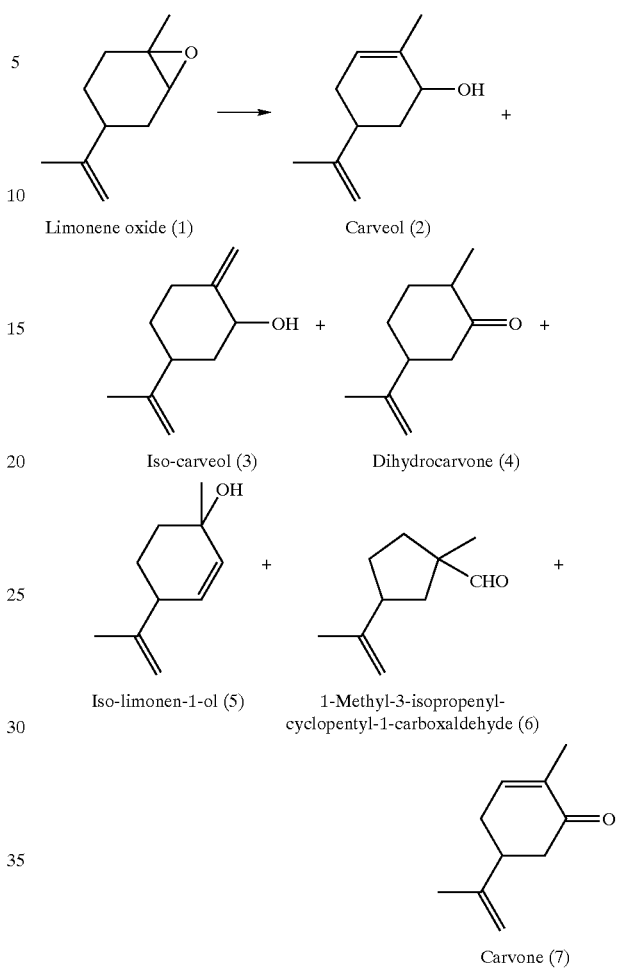

Scheme 1

It is generally accepted that proton abstraction in the rearrangement of epoxides to allylic alcohols occurs at the least substituted carbon (J. Gorzynsky Smith, Synthetically useful reactions of epoxides, Synthesis, 1984, (8), pp. 629–656, which is incorporated by reference in its entirety).

According to this rule in the rearrangement of 1,2-limonene oxide (1, see scheme 1) promoted by strong bases a preferential formation of iso-carveol (3) occurs (Y. Bessiere and R. Derguini-Boumechal, J. Chem. Res. (S), 1977, (12), pp. 304–305). The highest selectivity to carveol (2), which is a flavor component and an intermediate in synthesis of carvone (7), was 22%.

B. Homogeneous Catalytic Rearrangement of Epoxides in the Presence of Metal Alkoxides.

The most widely used catalysts in this group are aluminum isopropoxide (E. H. Eschinasi, Isr. J. Chem., 1968, 6, pp. 713–721), titanium alkoxides (JP 50/58031, English translation of the full text), and zirconium butoxide (U.S. Pat. No. 4,496,776), all of which are incorporated by reference in their entirety.

In the presence of these catalysts the selectivity of 1,2-limonene oxide rearrangement to carveol is between 24% (aluminum isopropoxide) and 60% (titanium isobutoxide). Common disadvantages of these catalysts are complicated work-up of the reaction mixtures, and low activity and selectivity, which limits their applications.

C. Heterogeneous Catalytic Rearrangement.

Numerous heterogeneous catalysts have been suggested for the conversion of epoxide to allylic alcohols. They include:

a) Metal oxides, specifically different grades of alumina, silica, titania, zirconia and mixed oxides (see review by K. Tanabe, R. Ohnishi, K. Arata, "Rearrangement of epoxides over solid acid and base catalysts", chapter 2.5 in: Terpene Chemistry, ed. J. Varghese. Tata McGraw-Hill Publishing Company, Ltd., 1982, pp. 67–88, and references therein, each of which are incorporated by reference). The highest selectivity achieved in 1,2-limonene oxide rearrangement to carveol catalyzed by metal oxides was 59% over aluminum oxide (K. Arata, K. Tanabe, Chem. Letters, 1976, pp. 321–322 which is incorporated by reference).

b) Metal phosphates. Commercial method for production of allyl alcohol is based on propylene oxide rearrangement in the presence of lithium phosphate (U.S. Pat. No. 2,426,624 and U. S. Pat. No. 2,986,585 which are incorporated by reference). The process is carried out at 275–300° C. The selectivity of allyl alcohol formation is about 80%. Lithium phosphate supported on silica (U.S. Pat. No. 5,455,215) and sodium phosphate supported on zirconia (JP 11/49709) were also used to effect the rearrangement of epoxides. Rearrangement of 1,2-limonene oxide in the presence of lithium phosphate was studied by S. G. Traynor et al. (Proceedings of The VIII International Congress of Essential Oils. Fedarom, Grasse, 1980, pp. 591–594). The reaction was very slow. The selectivity of trans-1,2-limonene oxide transformation to cis-carveol was 18.1% at 66.2% conversion (57 hours, 200° C.).

The selectivity of cis-1,2-limonene oxide transformation to trans-carveol was 13.6% at 69.9% conversion (57 hours, 200° C.). In this reaction a significant amount of carbonyl compounds—aldehyde (6) and ketone (4)—was produced (10.9% and 4.3% respectively). The major product was iso-carveol (3)—68.7% in case of cis-1,2-limonene oxide rearrangement and 59.9% in case of trans-1,2-limonene oxide rearrangement. Each of the above-discussed documents are incorporated by reference in their entirety.

As can be seen, traditional methods for epoxide rearrangement to allylic alcohols fail to selectively produce carveol from 1,2-limonene oxide.

It was reported that in some cases preparation of allylic alcohols from epoxides is accompanied by formation of a significant amount of the corresponding unsaturated carbonyl compound.

For example, in the rearrangement of 1,2-limonene oxide over metal oxides and binary oxides, the selectivity of carvone (7) formation was as high as 35% at 75% conversion of epoxide. However, total selectivity to carveol and carvone was only 59% (J. Jayasree, Ind. J. Chem., 1997, Vol. 36A, (9), pp. 765–768). Formation of unsaturated carbonyl compounds during the rearrangement of epoxides results from the Oppenauer oxidation of the allylic alcohol. This reaction is possible because (i) some epoxide rearrangement catalysts are also capable of catalyzing the Oppenauer oxidation; and (ii) by-products of the rearrangement—dihydrocarvone (4) and aldehyde (6) in the discussed example—can act as hydrogen acceptors. It is clear that the more alpha,beta-unsaturated compound is produced, the lower is total yield of allylic alcohol and alpha,beta-unsaturated carbonyl compound, since more epoxide undergoes undesired transformation to the corresponding carbonyl compounds (4 or 6) and further to saturated alcohols (8) or (9). The sequence of the epoxide rearrangement and the Oppenauer oxidation of allylic alcohol utilizing carbonyl by-products as hydrogen acceptors is presented in scheme 2.

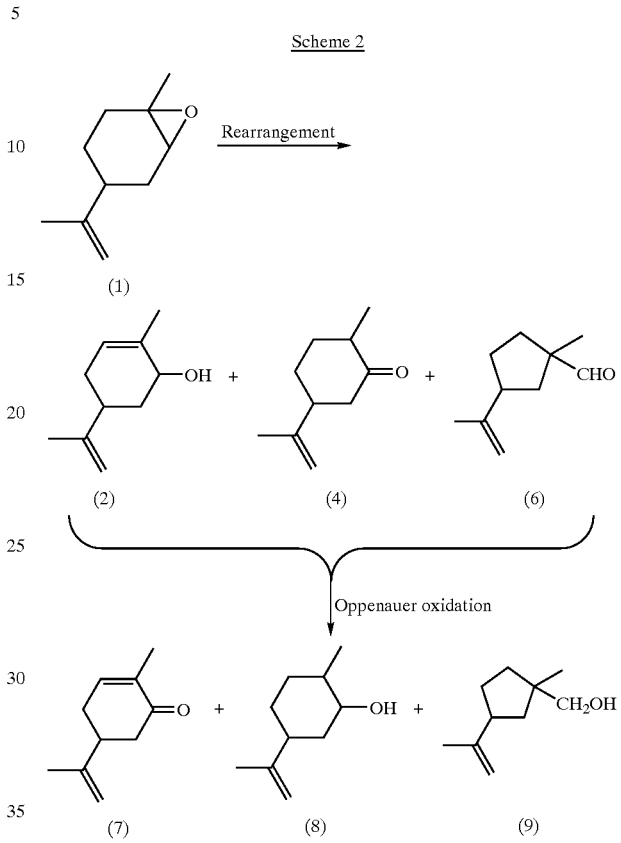

Scheme 2

In many instances preparation of alpha, beta-unsaturated carbonyl compounds from epoxides by the sequence of rearrangement and oxidation reactions is an ultimate goal. Yet, none of the traditional techniques is capable of combining these two steps to produce high yields of alpha, beta-unsaturated carbonyl compound, particularly in a one-pot process.

SUMMARY OF THE INVENTION

The present invention is based in part on the discovery that the inclusion of certain activator/modifier(s) in a catalyst system can significantly improve the activity and/or selectivity of the catalyst system, particularly in connection with the rearrangement of epoxides. For example, it has now been found that variety of allylic alcohols can be selectively produced by rearrangement of corresponding epoxides in the presence of the catalyst system that comprises primary catalyst and activator/modifier.

Among other aspects, the present invention includes a catalyst system that can be used to achieve:

a) preparation of allylic alcohols by rearrangement of the corresponding epoxide, when the allylic alcohol is a desired product;
b) subsequent reaction, e.g., selective oxidation, of the allylic alcohols obtained in step (a) to afford a desired product, e.g., alpha, beta-unsaturated carbonyl compounds; and/or c) the ability to perform steps a) and b) in a one-pot process.

The primary catalyst can be selected from homogeneous or heterogeneous, organic, inorganic or complex metal compounds including oxides, hydroxides, carbonates, carboxylates, acetylacetonates among others.

The activator/modifier can be selected from a wide array of phenolic compounds including phenol, hydroxyphenols, mono- and poly-substituted alkyl phenols, alkoxyphenols, aminophenols, nitrophenols, hydroxyacetophenones, salicylic acid and its derivatives, para-hydroxybenzoic acid and its derivatives, among others.

In one embodiment, the present invention can be employed in the manufacture of high quality fragrance and flavor grade products such as isomers of carveol and carvone.

DETAILED DESCRIPTION OF THE INVENTION

The catalyst system according to present invention includes the following components: (i) one or more primary catalysts and (ii) one or more phenolic activator/modifiers.

The primary catalyst component can be homogeneous or heterogeneous, inorganic, organic or complex compound including, but not limited to, metal oxides, hydroxides, carbonates, carboxylates, acetylacetonates, and the like.

Specific examples of suitable heterogeneous inorganic primary catalysts include but are not limited to: magnesium oxide, calcium oxide, barium oxide, zinc oxide, lithium hydroxide, magnesium hydroxide, calcium hydroxide, barium hydroxide, calcium carbonate, zinc carbonate, cobalt carbonate, copper carbonate, nickel carbonate, zirconium carbonate.

Specific examples of suitable homogeneous organic and complex primary catalysts include but are not limited to: zinc acetate, zinc octoate (2-ethylhexanoate), zinc stearate, zinc acetylacetonate, calcium stearate, cobalt naphthenate, iron octoate, copper naphthenate, copper octoate, nickel octoate, nickel naphthenate, chromium octoate, vanadium octoate, aluminum 2-ethylhexanoate.

The phenolic activator/modifier compounds are selected to affect the primary catalyst in one of two ways.

First, phenolic compounds can perform as activators for the primary catalyst compounds that are otherwise inactive in the desired, e.g., epoxide rearrangement, reactions. This beneficial effect allows employing a variety of catalysts that were previously not employed in the rearrangement of epoxides.

Second, the phenolic compounds can act as selectivity modifiers for catalyst compounds that are active themselves. This beneficial effect allows for the selectivity to be more effectively controlled and the reaction to be carried out in the desired direction.

According to present invention numerous combinations of primary catalysts and phenolic activator/modifier are possible. This opens the opportunity for custom tailoring and fine-tuning the catalyst activity and selectivity to produce high yields of the targeted allylic alcohols.

Examples of suitable phenolic compounds include but are not limited to: phenol, mono-alkylphenols (cresols, isopropylphenols, tert-butylphenols, nonylphenol), di-alkylphenols (di-methylphenols, di-tert-butylphenols, carvacrol, thymol), chlorophenols, hydroxyphenols (pyrocatechol, hydroquinone), alkoxyphenols (guiacol, di-methoxyphenol), butylhydroxytoluene, nitrophenols, aminophenols, salicylic acid and its derivatives (esters, amide), and hydroxyacetophenone.

Preferred examples of the catalyst system include but are not limited to the following combinations of primary catalyst and activator/modifier: magnesium hydroxide and carvacrol, calcium hydroxide and carvacrol, calcium hydroxide and thymol, calcium hydroxide and 2-hydroxyacetophenone, calcium oxide and isoamyl salicylate, calcium oxide and benzyl salicylate, calcium oxide and isopropyl salicylate, zinc carbonate and carvacrol, zinc carbonate and 2-aminophenol, zinc carbonate and 2-nitrophenol, zinc octoate and 2-nitrophenol, zinc octoate and 2-aminophenol, zinc acetylacetonate and 2-nitrophenol.

The components of the catalyst system can be added to epoxide separately, in any sequence, or the catalyst system can be pre-blended prior to introduction into the reaction mixture.

The amount of phenol activator/modifier employed in the reaction mixture is selected to provide the desired activation/selectivity function. In particular, the preferred amount of phenol activator/modifier is that amount effective to improve the activity and/or selectivity of the primary catalyst in the rearrangement of a desired starting material, e.g., epoxide to a product, e.g., an allylic alcohol, as compared to the use of the primary catalyst without the activator/modifier.

For certain preferred epoxide rearrangements, a preferred concentration of catalyst and activator/modifier is 0.05–10% and 0.025–10% weight percent based on the epoxide. However, depending on activity of epoxide and the catalyst system, lower or even higher amounts can be used.

The reaction typically does not require a solvent. However, when desired, an appropriate solvent that is inert to starting materials, e.g., epoxides, and intermediate or final products, e.g., allylic alcohols, under reaction conditions can be used. The examples of solvent are illustrated by but not limited to hydrocarbons, ethers, amides, sulfoxides, and the like.

In addition, other additives that do not adversely effect the desired rearrangement can also be present in the reaction mixture depending on the nature of the desired reaction.

According to present invention a wide range of epoxides can be converted to allylic alcohols. Examples of terminal, cyclic, di-substituted, tri-substituted epoxides are 1,2-limonene oxide, 8,9-limonene oxide, alpha-pinene oxide, beta-pinene oxide, 2,3-carene oxide, 3,4-carene oxide, 1,2-terpinolene oxide, 4,8-terpinolene oxide, sylvestrene oxide, 1,2-menthene oxide, 2,3-menthene oxide, 3,4-menthene oxide, 7,8-dihydromyrcene oxide, caryophyllene oxide, 1,2-epoxycyclododecane, and the like.

The rearrangement of epoxides to allylic alcohols according to present invention can be carried out by contacting epoxide with catalyst system under suitable reaction conditions, e.g., at elevated temperature, usually at reflux. The epoxide rearrangement can be performed in a batch or continuous mode.

Other suitable steps can also be included in the rearrangement process. For example, it can be preferable to remove water containing in starting materials or formed in the process. In such instances, water can be removed before or in the course of rearrangement by known methods.

When an allylic alcohol is a final product, the rearrangement can be stopped, e.g., after all epoxide is reacted or the desired conversion is achieved.

Moreover, steps subsequent to the rearrangement can be employed. For example, the catalyst can be removed by any appropriate method (filtration, wash, extraction, distillation, etc.) and the product, e.g., allylic alcohol, can be isolated and purified using any art recognized procedure (distillation, crystallization, boration, etc.).

Under the preferred rearrangement conditions according to present invention, obtained allylic alcohols retain the optical activity of its parent epoxide. For example, in one preferred embodiment of the invention, the rearrangement of R-(+)-1,2-limonene epoxide affords R-(−)-carveol and, further, R-(−)-carvone. Correspondingly, the rearrangement of S-(−)-1,2-limonene oxide affords S-(+)-carveol and, further, S-(+)-carvone.

By choosing an appropriate combination of primary catalyst and activator/modifier high regioselectivity can be achieved. For example, in the preferred embodiment, starting with 1,2-limonene oxide carveol can be produced with 84–87% selectivity in the presence of calcium oxide/isopropyl salicylate or zinc oxide/2-aminophenol, while iso-carveol can be obtained from the same feed stock with 80% selectivity by using chromium octoate and 2-aminophenol.

The catalyst system according to present invention can also be active in a subsequent reaction of the allylic alcohols, e.g., the Oppenauer oxidation of allylic alcohols formed in the epoxide rearrangement reaction. Thus, another aspect of the invention relates to the use of the allylic alcohol as an intermediate, e.g., an intermediate in the synthesis of alpha, beta-unsaturated carbonyl compound. In such processes, the rearrangement and the oxidation steps can be performed simultaneously as two parallel independent processes.

In addition, other suitable steps can be included in such a process. For example, where the process includes an Oppenauer oxidation step, the presence of hydrogen acceptor—an auxiliary carbonyl compound can be needed (see C. Djerasse, "The Oppenauer oxidation" in: Organic Reactions, John Wiley and Sons, Inc., New York, 1951, Vol. VI, Chapter 5, pp. 207–272, and C. F. de Graauw et al., Synthesis, 1994, (10), 1007–1017 which is incorporated by reference). Thus, in the present invention, a hydrogen acceptor can be added to the reaction mixture to induce the Oppenauer oxidation reaction. In this case hydrogen acceptor can be added at the beginning or in the course of the combined rearrangement-oxidation process.

Examples of hydrogen acceptors suitable for the Oppenauer oxidation according to present invention include, but are not limited to cyclohexanone, 2-ethylhexanal, dihydrocarvone, benzaldehyde, furfural, and the like.

The Oppenauer oxidation is also a reversible process. To complete the reaction, it is desirable to remove one of the products. Usually the boiling point of the alcohol formed from hydrogen acceptor is higher than the boiling point of hydrogen acceptor itself. For this reason, according to present invention hydrogen acceptor is added in increments. After addition of each increment of hydrogen acceptor the reaction mixture is allowed to equilibrate, then unreacted hydrogen acceptor and formed alcohol are removed by distillation. Incremental addition of hydrogen acceptor should be continued until desired conversion of allylic alcohol to alpha, beta-unsaturated carbonyl compound is achieved.

The technique of incremental addition of auxiliary carbonyl compound with periodical removal of related to it alcohol allows to achieve high conversion (above 95%) of starting alcohol at low molar ratio between starting alcohol or epoxide and auxiliary carbonyl compound. Typically, this ratio is between about 1:0.7 and 1:1.5. In addition, this technique allows to minimize side reactions (aldol condensation, Tishchenko reaction, etc.) of the auxiliary carbonyl compound.

The multiple reaction steps, e.g., rearrangement and the Oppenauer oxidation, can be performed in succession as one-pot two step process. In this case hydrogen acceptor is preferably added to the reaction mixture after the rearrangement step is completed.

By "one-pot", it is meant that the reaction can occur in a single reaction system. To this end, the apparatus is not critical and any apparatus suitable for use in the multiple reaction steps can be employed.

When the epoxide rearrangement or combined rearrangement/oxidation process is complete, the catalyst can be conveniently removed by filtration, distillation, extraction, etc. Alternatively, the target product can be isolated and purified by appropriate methods without removing the catalyst.

One particularly preferred environment in which the present invention can be employed relates to the formation of fragrance and flavor grade products. For example, after purification the purity of R-(−)-carvone and S-(+)-carvone can be 99.6–99.8% (even higher purity individual cuts can be isolated) with dihydrocarvone (0.1–0.3%) as major impurity.

Commercially available synthetic R-(−)-carvone made by traditional "nitrosyl chloride" method ("The Chemistry of Fragrances", The Royal Society of Chemistry, 1999, pp. 69–69) contains alpha-terpineol and octanol as main impurities. Usually, users of carvone add dihydrocarvone, an expensive ingredient, separately to imitate the natural spearmint oil. Therefore, carvone obtained in accordance with the invention can be superior to product currently in the market. In addition, carvone produced according to present invention is more color stable, which provides enhanced utility. Thus, the invention can offer a convenient and practical catalyst system and process for regio- and stereoselective preparation of allylic alcohols and/or alpha, beta-unsaturated carbonyl compounds by rearrangement of epoxides or by combined epoxide rearrangement-Oppenauer oxidation process.

The following examples illustrate certain specific examples of the invention however, those skilled in art should understand that these examples do not limit the scope of the invention.

EXAMPLES 1–33

Rearrangement of 1,2-Limonene Oxide (Activation of Heterogeneous Catalysts by Phenolic Compounds)

A mixture of 1,2-limonene oxide (65% cis isomer and 35% trans isomer), the catalyst and the phenolic compound (amounts are specified in table 1) was heated up to reflux (usually 200–230° C.) in a flask equipped with a stirrer, thermometer, Dean-Stark trap, and condenser. Water collected in a Dean-Stark trap was removed. Periodically the reaction mixture was sampled and analyzed by GC on a polar 30-meter capillary column. Term ND in table 1 indicates that the corresponding product was not detected by GC.

TABLE 1

| Exam. No. | Catalyst | Catalyst Wt. % | Phenolic Compound | Phenolic compound Wt. % | Time hours | 1,2-LMO conversion, % | Selectivity, % (2) | (3) | (7) |
|---|---|---|---|---|---|---|---|---|---|
| 1 | Calcium oxide | 3.0 | None | — | 5 | ND | ND | ND | ND |
| 2 | Calcium oxide | 2.3 | Isopropyl salicylate | 4.0 | 6 | 74.5 | 84 | 6 | 2 |
| 3 | Calcium oxide | 2.0 | Amyl salicylate | 3.8 | 7.5 | 76.9 | 83 | 5 | 2 |
| 4 | Calcium oxide | 2.5 | Benzyl salicylate | 3.8 | 5 | 78.4 | 71 | 6 | 5 |
| 5 | Calcium hydroxide | 3.0 | None | — | 5 | ND | ND | ND | ND |
| 6 | Calcium hydroxide | 2.0 | Carvacrol | 2.0 | 4 | 81.1 | 69 | 13 | 4 |
| 7 | Calcium hydroxide | 2.0 | Thymol | 2.0 | 7 | 82.7 | 63 | 12 | 8 |
| 8 | Calcium hydroxide | 2.0 | Guaiacol | 3.0 | 8 | 59.5 | 59 | 9 | 9 |
| 9 | Calcium hydroxide | 2 | ortho-cresol | 1.3 | 5 | 84.7 | 54 | 12 | 12 |
| 10 | Calcium hydroxide | 2.0 | 2,6-dimethyl phenol | 1.7 | 5 | 82.1 | 50 | 12 | 12 |
| 11 | Calcium hydroxide | 2.0 | 2,4-di-tert.-butyl phenol | 1.5 | 8 | 55.8 | 57 | 23 | 4 |
| 12 | Calcium hydroxide | 2.0 | p-tert.-butyl phenol | 3.0 | 10 | 70.2 | 65 | 16 | 4 |
| 13 | Calcium hydroxide | 2.0 | 2,4-dichloro-phenol | 1.8 | 6 | 34.4 | 40 | 6 | 9 |
| 14 | Calcium hydroxide | 2.0 | 2-sec.-butyl phenol | 2 | 6 | 67.6 | 68 | 16 | 3 |
| 15 | Calcium hydroxide | 2.0 | o-hydroxy-phenol | 2.0 | 1 | 71 | 62 | 16 | 8 |
| 16 | Calcium carbonate | 6.7 | None | — | 5 | ND | ND | ND | ND |
| 17 | Calcium carbonate | 6.7 | Carvacrol | 6.7 | 12 | 66.8 | 27 | 13 | 2 |
| 18 | Magnesium oxide | 5.0 | None | — | 5 | ND | ND | ND | ND |
| 19 | Magnesium oxide | 2.0 | Phenyl salicylate | 2.0 | 7.5 | 49.5 | 50 | 13 | 3 |
| 20 | Magnesium hydroxide | 3.3 | None | — | 6 | 4.0 | 54 | 18 | 3 |
| 21 | Magnesium hydroxide | 4.0 | Phenol | 3.5 | 4 | 94.5 | 50 | 23 | 9 |
| 22 | Magnesium hydroxide | 2.0 | Carvacrol | 6.0 | 6 | 96.0 | 43 | 21 | 9 |
| 23 | Lithium hydroxide | 1.0 | None | — | 3 | 68.6 | 32 | 21 | 7 |
| 24 | Lithium hydroxide | 1.0 | Phenol | 2.7 | 7 | 62.6 | 44 | 12 | 8 |
| 25 | Cobalt carbonate | 6.7 | None | — | 4 | 20.6 | 42 | 21 | 2 |
| 26 | Cobalt carbonate | 6.7 | Carvacrol | 6.7 | 4 | 91.0 | 32 | 23 | 12 |
| 27 | Barium oxide | 3.0 | None | — | 3 | ND | ND | ND | ND |
| 28 | Barium oxide | 3.0 | Carvacrol | 2.0 | 1 | 63.6 | 10 | 4 | 2 |
| 29 | Zinc oxide | 2.0 | None | — | 6 | ND | ND | ND | ND |
| 30 | Zinc oxide | 2.0 | 2-amino-phenol | 0.8 | 6 | 66.0 | 87 | 7 | 1 |
| 31 | zinc carbonate | 3.0 | None | — | 3 | ND | ND | ND | ND |
| 32 | zinc carbonate | 1.7 | 2-nitro-phenol | 0.85 | 5 | 99.7 | 64 | 5 | 14 |
| 33 | zinc carbonate | 1.0 | 2-amino-phenol | 1.8 | 3 | 100 | 78 | 4 | 7 |

EXAMPLES 34–47

Rearrangement of 1,2-Limonene Oxide

This set of examples illustrates the effect of phenolic compounds on activity and selectivity of homogeneous catalysts. Same general procedure as in examples 1–33 was employed.

TABLE 2

| Exam. No. | Catalyst | Catalyst Wt. % | Phenolic Compound | Phenolic compound Wt. % | Time hours | 1,2-LMO conversion % | Selectivity, % (2) | (3) | (7) |
|---|---|---|---|---|---|---|---|---|---|
| 34 | Zinc acetate | 1 | None | — | 8 | 45.5 | 27 | 20 | 17 |
| 35 | Zinc acetate | 1 | 2-nitro-phenol | 0.83 | 4 | 95.7 | 48 | 10 | 20 |
| 36 | Zinc octoate | 1.3 | None | — | 2 | 84.3 | 16 | 24 | 19 |
| 37 | Zinc octoate | 1.3 | 2-nitro-phenol | 0.65 | 5 | 99.1 | 58 | 8 | 16 |
| 38 | Zinc octoate | 0.28 | 2-amino-phenol | 0.12 | 2.5 | 100 | 74 | 6 | 10 |
| 39 | Zinc octoate | 0.14 | 2-amino-phenol | 0.06 | 4 | 99.8 | 70 | 7 | 13 |
| 40 | Calcium octoate | 0.3 | None | — | 10 | 19.0 | 35 | 13 | 17 |
| 43 | Calcium octoate | 1.0 | Isopropyl salicylate | 0.5 | 10 | 53.4 | 70 | 7 | 7 |
| 44 | Chromium Octoate | 1.7 | None | — | 3 | 99.4 | 5 | 73 | 1 |
| 45 | Chromium Octoate | 1.7 | 2-amino-phenol | 0.5 | 2.5 | 99.5 | 6 | 80 | 1 |
| 46 | Zinc acetyl-acetonate | 2.0 | None | — | 3 | 63.7 | 22 | 48 | 10 |
| 47 | Zinc acetyl-acetonate | 2.0 | 2-nitro-phenol | 1.0 | 3 | 97.0 | 47 | 11 | 22 |

EXAMPLES 48–53

Rearrangement of 1,2-Limonene Oxide

This set of examples illustrates applicability of different classes of solvents in epoxide rearrangements according to present invention.

General procedure: a mixture of 20 parts of 1,2-limonene oxide (65% cis and 35% trans-isomer), 20 parts of solvent (see table 3), 0.36 parts of zinc carbonate, and 0.18 parts of 2-nitrophenol was refluxed for a specified period of time (see table 3). Water was removed using Dean-Stark trap.

TABLE 3

| Example number | Solvent | Time, hours | Conversion, % | Selectivity to (2) + (7), % |
|---|---|---|---|---|
| 48 | Hexadecane | 2 | 36.8 | 75.1 |
| 49 | Diphenyl ether | 1 | 44.3 | 77.5 |
| 50 | Tetra(ethylene glycol) dimethyl ether | 1.5 | 44.6 | 75.0 |
| 51 | N-Methylpyrrolidone | 8 | 44.0 | 67.0 |
| 52 | Sulfolane | 2 | 68.2 | 64.7 |
| 53 | Tri-Ethylene glycol | 3 | 40 | 39.0 |

EXAMPLE 54

Preparation of R-(−)-Carveol

A mixture of 1500 parts of R-(+)-1,2-limonene oxide (cis to trans ratio 65:35), 2.4 parts zinc octoate (18% zinc) and 1 parts 2-aminophenol was refluxed at 202–225° C. for 3 hours in a 3-L flask equipped with thermocouple, agitator and Dean-Stark trap. About 1.5 parts water was removed. After cooling, 1495 parts of crude R-(−)-carveol was obtained. This product contains 0.3% limonene oxide, 75.2% R-(−)-carveol (total of cis and trans isomers), and 9.4% R-(−)-carvone. The theory yield of R-(−)-carveol is 75%. The theory yield of R-(−)-carvone is 9.3%, and the total yield of R-(−)-carveol and R-(−)-carvone is 84.3%. This mixture can be used for R-(−)-carvone preparation without further purification. Distillation of crude R-(−)-carveol obtained by this procedure on a packed column (40–50 theory plates) under vacuum affords 98% pure R-(−)-carveol or better.

EXAMPLE 55

Preparation of R-(−)-Carveol using Recycle Catalyst

Crude R-(−)-carveol obtained according to Example 54 was distilled under vacuum using Vigreux column. The residue after distillation was combined 1500 parts of R-(+)-1,2-limonene oxide, and catalyst make-up (0.2 g zinc octoate and 0.1 g 2-aminophenol). The rearrangement was carried out according to Example 54 affording same results as in Example 54.

EXAMPLE 56

Preparation of R-(−)-Carvone (One-Pot Simultaneous Rearrangement of R-(+)-1,2-Limonene Oxide and Oppenauer Oxidation of R-(−)-Carveol in the Presence of Magnesium Hydroxide—Carvacrol Catalyst System)

A mixture of 100 parts of R-(+)-1,2-limonene oxide, 75 parts of dihydrocarvone, 3 parts of carvacrol and 1 part magnesium hydroxide was refluxed at 212–220° C. for 10 hours in a three-necked flask equipped with agitator, temperature probe, and Dean-Stark trap (about 1 part water was removed). The reaction mixture was cooled down to 40° C., the catalyst was flittered out and the filtrate distilled under vacuum using Vigreux column. Distillate (160 parts) contains 28% unreacted 1,2-limonene oxide and 31% R-(−)-carvone. The yield of R-(−)-carvone is 49.6 parts or 68.8% on reacted 1,2-limonene oxide. This mixture was further purified using conventional separation techniques to obtain flavor grade R-(−)-carvone.

EXAMPLE 57

Preparation of R-(−)-Carvone. (One-Pot Successive Rearrangement of R-(+)-1,2-Limonene Oxide and Oppenauer Oxidation of R-(−)-Carveol in the Presence of Zinc Carbonate—2-Nitrophenol Catalyst System.)

A mixture of 600 parts of R-(+)-1,2-limonene oxide, 5.7 parts of 2-nitrophenol and 12 parts of zinc carbonate was refluxed at 202–227° C. for 7 hours in a three-necked flask equipped with agitator, 3-foot distillation column, distillation head, temperature probe, and addition funnel. When the rearrangement step was completed (no 1,2-limonene oxide left in the reaction mixture), 190 parts of cyclohexanone were slowly added to the reaction mixture. The mixture was held at reflux for 2 hours at 195–200° C. and then cooled down to 120° C. The mixture of cyclohexanone and cyclohexanol was removed at 10–15 mm Hg and pot temperature below 120° C. Cyclohexanone addition step followed by reflux and removal of cyclohexanone-cyclohexanol mixture under vacuum was repeated two more times. After the oxidation step was completed, the conversion of R-(−)-carveol to R-(−)-carvone was above 95%. The catalyst was removed by filtration, and the filtrate was distilled to afford 473 parts of 80% pure R-(−)-carvone (theory yield 63% on 1,2-limonene oxide). This material was purified using conventional methods to 99.6% pure flavor grade R-(−)-carvone.

EXAMPLE 58

Preparation of R-(−)-Carvone. (One-Pot Successive Rearrangement of R-(+)-1,2-Limonene Oxice and Oppenauer Oxidation of R-(−)-Carveol in the Presence of Zinc Octoate—2-Aminophenol Catalyst System.)

A mixture of 600 parts of R-(+)-1,2-limonene oxide, 0.5 parts of 2-aminophenol and 1 part of zinc octoate (contains 22% zinc) was refluxed at 202–227° C. for 2 hours in a three-necked flask equipped with agitator, 3-foot distillation column, distillation head, temperature probe, and addition funnel. When the rearrangement step was completed, the reaction mixture was cooled down to 190° C., and 3 parts of zinc octoate and 190 parts of cyclohexanone were added. The oxidation step was carried out as it was described in example 57, except the pot contents were distilled without filtration. The distillation afforded 534 parts of 82% pure R-(−)-carvone (theory yield 73% on 1,2-limonene oxide). This material was purified using conventional methods to obtain flavor grade R-(−)-carvone.

EXAMPLE 59

Continuous Rearrangement of 1,2-Limonene Oxide

A mixture of 95% of 1,2-limonene oxide and 5% of carvacrol was continuously fed through a pre-heater into a tubular reactor packed with calcium hydroxide at the rate of 1 part of 1,2-limonene oxide per 1 part catalyst per hour. The temperature maintained at 230–250° C. with an external heater. The pressure in the reactor maintained at 30–50 psig. A rearrangement product containing 6% unreacted epoxide, 44% carveol and 11% carvone was collected. The total selectivity to carvone and carveol was 58.5%.

EXAMPLE 60

Rearrangement of Cis-1, 2-Limonene Oxide

A mixture of 1000 parts of cis-1,2-limonene oxide, 1 part of zinc octoate (contains 18% zinc) and 0.5 parts of 2-aminophenol was refluxed at 200–225° C. for 1.5 hours in a three-necked flask equipped agitator, Dean-Stark trap, and temperature probe. This process is exothermic. Cooling should be applied to prevent a runaway reaction. After cooling 998 part of the mixture containing 87% carveol and 3% carvone was obtained. This mixture can be further processed to carvone according to example 58, or fractionated to obtain pure trans-carveol.

EXAMPLE 61

Rearrangement of Trans-1,2-Limonene Oxide

A mixture of 1000 parts of trans-1,2-limonene oxide, 4 parts of zinc octoate (contains 18% zinc) and 2 parts of 2-aminophenol was refluxed at 200–226° C. for 3 hours in a three-necked flask equipped agitator, Dean-Stark trap, and temperature probe. After cooling 998 part of the mixture containing 67% carveol and 8% carvone was obtained. This mixture can be further processed to carvone according to example 58, or fractionated to obtain pure cis-carveol.

EXAMPLE 62

Rearrangement of 8,9-Limonene Oxide

A mixture of 300 parts of 8,9-limonene oxide, 6 parts of calcium hydroxide and 6 parts of carvacrol was refluxed at 215–230° C. for 2 hours in a three-necked flask equipped agitator, Dean-Stark trap, and temperature probe. After cooling and filtration 290 parts of the mixture containing 30% of unreacted epoxide and 43% 1,8-p-menthadien-10-ol (61% selectivity) was obtained.

EXAMPLE 63

Rearrangement of 1,2-Epoxidodecane

A mixture of 180 parts of trans-1,2-epoxidodecane, 6 parts of calcium hydroxide and 0.3 parts of o-hydroxyacetophenone was refluxed at 210–220° C. for 3 hours in a three-necked flask equipped agitator, Dean-Stark trap, and temperature probe. After cooling and filtration 175 parts of the mixture containing 15% starting epoxide and 74% cyclododec-2-en-1-ol (85% conversion, 87% selectivity) was obtained.

EXAMPLE 64

Preparation of S-(+)-Carvone. (One-Pot Successive Rearrangement of S-(−)-1,2-Limonene Oxide and Oppenauer Oxidation of S-(+)-Carveol in the Presence of Zinc Octoate—2-Aminophenol Catalyst System.)

The process was carried out under conditions of example 58 except S-(−)-limonene oxide was used as starting material, and flavor quality S-(+)-carvone was obtained.

Each of the above-mentioned publications, including articles, patents, etc., are incorporated by reference in their entirety for all purposes.

While the present invention has been described in terms of various preferred embodiments thereof, it is to be understood that various modifications, changes, substitutions, omissions, alterations, and the like may be made without departing from the spirit thereof.

We claim:

1. A catalyst system for use in the rearrangement of epoxides to allylic alcohols, comprising:
   a) at least one primary catalyst comprising at least one metal oxide, metal carbonate, metal carboxylate, metal acetylacetonate, calcium hydroxide, magnesium hydroxide, or barium hydroxide; and
   b) at least one activator/modifier comprising at least one phenolic compound, wherein the activator/modifier is present in an amount effective to improve the activity and/or selectivity of the primary catalyst in the rearrangement of an epoxide to an allylic alcohol as compared to the use of the primary catalyst without the activator/modifier.

2. The catalyst system according to claim 1, wherein the at least one phenolic compound comprises a phenol, a mono- or polysubstituted alkylphenols, a nitrophenols, an aminophenols, an hydroxyphenols, an alkoxyphenols, an hydroxyacetophenones, a salicylic acids or a derivative of salicylic acid.

3. The catalyst system of claim 1, wherein the at least one primary catalyst comprises a metal carboxylate.

4. The catalyst system of claim 1, wherein the at least one activator/modifier comprises an aminophenol.

5. The catalyst system of claim 1, wherein the at least one primary catalyst comprises magnesium hydroxide and the at least one activator/modifier comprises carvacrol.

6. The catalyst system of claim 1, wherein the at least one primary catalyst comprises calcium hydroxide and the at least one activator/modifier comprises carvacrol.

7. The catalyst system of claim 1, wherein the at least one primary catalyst comprises calcium hydroxide and the at least one activator/modifier comprises thymol.

8. The catalyst system of claim 1, wherein the at least one primary catalyst comprises calcium hydroxide and the at least one activator/modifier comprises 2-hydroxyacetophenone.

9. The catalyst system of claim 1, wherein the at least one primary catalyst comprises calcium oxide and the at least one activator/modifier comprises isoamyl salicylate.

10. The catalyst system of claim 1, wherein the at least one primary catalyst comprises calcium oxide and the at least one activator/modifier comprises benzyl salicylate.

11. The catalyst system of claim 1, wherein the at least one primary catalyst comprises calcium oxide and the at least one activator/modifier comprises isopropyl salicylate.

12. The catalyst system of claim 1, wherein the at least one primary catalyst comprises zinc carbonate and the at least one activator/modifier comprises carvacrol.

13. The catalyst system of claim 1, wherein the at least one primary catalyst comprises zinc carbonate and the at least one activator/modifier comprises 2-aminophenol.

14. The catalyst system of claim 1, wherein the at least one primary catalyst comprises zinc carbonate and the at least one activator/modifier comprises 2-nitrophenol.

15. The catalyst system of claim 1, wherein the at least one primary catalyst comprises zinc octoate and the at least one activator/modifier comprises 2-nitrophenol.

16. The catalyst system of claim 1, wherein the at least one primary catalyst comprises zinc octoate and the at least one activator/modifier comprises 2-aminophenol.

17. The catalyst system of claim 1, wherein the at least one primary catalyst is zinc octoate and the at least one activator/modifier is 2-aminophenol.

18. The catalyst system of claim 1, wherein the at least one primary catalyst comprises zinc acetylacetonate and the at least one activator/modifier comprises 2-nitrophenol.

19. The catalyst system of claim 1, wherein the at least one primary catalyst is present in an amount in the range of from 0.05 weight percent to 10 weight percent relative to an epoxide and the at least one activator/modifier is present in an amount in the range of from 0.025 weight percent to 10 weight percent relative to the epoxide.

20. The catalyst system of claim 2, wherein the salicylic acid derivative is an ester or an amide.

* * * * *